United States Patent
Pham et al.

[11] Patent Number: 5,423,829
[45] Date of Patent: Jun. 13, 1995

[54] ELECTROLYTICALLY SEVERABLE JOINT FOR ENDOVASCULAR EMBOLIC DEVICES

[75] Inventors: Phong Pham, Fremont; Hong Doan, Santa Clara; Ivan Sepetka, Redwood City, all of Calif.

[73] Assignee: Target Therapeutics, Inc., Fremont, Calif.

[21] Appl. No.: 147,529

[22] Filed: Nov. 3, 1993

[51] Int. Cl.⁶ .................................. A61B 17/00
[52] U.S. Cl. .......................... 606/108; 606/1; 604/57
[58] Field of Search ............. 606/1, 32, 41, 49, 28, 606/108, 194, 8; 128/772; 604/280, 281, 57

[56] References Cited

U.S. PATENT DOCUMENTS

| | | | |
|---|---|---|---|
| 3,868,958 | 3/1975 | Alfidi et al. | 606/194 |
| 4,512,338 | 4/1985 | Balko et al. | 606/108 |
| 4,739,768 | 4/1988 | Engelson | 604/281 X |
| 4,884,579 | 12/1989 | Engelson | 604/281 X |
| 4,994,069 | 2/1991 | Richart et al. | 606/191 |
| 5,108,407 | 4/1992 | Geremia et al. | 606/108 |
| 5,122,136 | 6/1992 | Guglielmi et al. | 606/32 |
| 5,250,071 | 10/1993 | Palermo | 606/198 |

Primary Examiner—Peter A. Aschenbrenner
Attorney, Agent, or Firm—Morrison & Foerster

[57] ABSTRACT

This invention is an apparatus for endovascular occlusion through the formation of thrombi in arteries, veins, aneurysms, vascular malformations, and arteriovenous fistulas. In particular, it deals with a sacrificial link between an endovascular device which is introduced to and is intended to remain at the desired thrombus formation site and the device used to introduce the device. The invention further includes a method for introduction of the device and its electrolytic separation.

13 Claims, 4 Drawing Sheets

ELECTROLYTICALLY SEVERABLE JOINT FOR ENDOVASCULAR EMBOLIC DEVICES

FIELD OF THE INVENTION

This invention is an apparatus for endovascular occlusion through the formation of thrombi in arteries, veins, aneurysms, vascular malformations, and arteriovenous fistulas. In particular, it deals with a sacrificial link between an endovascular device which is introduced to and is intended to remain at the desired thrombus formation site and the device used to introduce the device. The invention further includes a method for introduction of the device and its electrolytic separation.

BACKGROUND OF THE INVENTION

Approximately 25,000 intracranial aneurysms rupture each year in North America. The primary purpose of treatment for a ruptured intracranial aneurysm is to prevent rebleeding. There are a variety of ways to treat ruptured and non-ruptured aneurysms.

Possibly the most widely known of these procedures is an extravascular approach using surgery or microsurgery. This treatment is common with intracranial berry aneurysms. The method comprises a step of clipping the neck of the aneurysm, performing a suture ligation of the neck, or wrapping the entire aneurysm. Each of these procedures is formed by intrusive invasion into the body and performed from the outside of the aneurysm or target site. General anesthesia, craniotomy, brain retraction, and placement of a clip around the neck of the aneurysm are typically required in these surgical procedures. The surgical procedure is often delayed while waiting for the patient to stabilize medically. For this reason, many patients die from the underlying disease or defect prior to the initiation of the procedure.

Another procedure—the extra-intravascular approach—involves surgically exposing or stereotactically reaching an aneurysm with a probe. The wall of the aneurysm is then perforated from the outside and various techniques are used to occlude the interior in order to prevent it from rebleeding. The techniques used to occlude the aneurysm include electrothrombosis, adhesive embolization, hog hair embolization, and ferromagnetic thrombosis. These procedures are discussed in U.S. Pat. No. 5,122,136 to Guglielmi et al., the entirety of which is incorporated by notice.

A still further approach is the least invasive and is additionally described in Guglielmi et al. It is the endovascular approach. In this approach, the interior of the aneurysm is entered by use of a catheter such as those shown in Engelson (Catheter Guidewire), U.S. Pat. No. 4,884,525 and also in Engelson (Catheter for Guidewire Tracking), U.S. Pat. No. 4,739,768. These patents describe devices utilizing guidewires and catheters which allow access to the aneurysm from remote portions of the body. Specifically by the use of catheters having very flexible distal regions and guidewires which are steerable to the region of the aneurysm, embolic devices which may be delivered through the catheter are an alternative to the extravascular and extra-intravascular approaches.

The endovascular approach typically includes two major sections. The first section involves the introduction of the catheter to the aneurysm site using devices such as shown in the Engelson patents. The second section often involves filling the aneurysm in some fashion or another. For instance, a balloon may be introduced into the aneurysm from the distal portion of the catheter where it is inflated, detached, and left to occlude the aneurysm. In this way, the parent artery is preserved. Balloons are becoming less in favor because of the difficulty in introducing the balloon into the aneurysm sac, the possibility of an aneurysm rupture due to overinflation of the balloon within the aneurysm, and the risk associated with the traction produced when detaching the balloon.

A highly desirable embolism-forming device which may be introduced into an aneurysm using endovascular placement procedures, is found in U.S. Pat. No. 4,994,069, to Ritchart et al. There is described a device—typically a platinum/tungsten alloy coil having a very small diameter—which may be introduced into an aneurysm through a catheter such as those described in Engelson above. These coils are often made of wire having a diameter of 2–6 mils. The coil diameter may be 10–30 mils. These soft, flexible coils may be of any length desirable and appropriate for the site to be occluded. For instance, the coils may be used to fill a berry aneurysm. Within a short period of time after the filling of the aneurysm with the embolic device, a thrombus forms in the aneurysm and is shortly thereafter complemented with a collagenous material which significantly lessens the potential for aneurysm rupture.

Coils such as seen in Ritchart et al. may be delivered to the vasculature site in a variety of ways including, e.g., mechanically detaching them from the delivery device as is shown in U.S. Pat. No. 5,250,071, to Palermo or by electrolytic detachment as is shown in Guglielmi et al. (U.S. Pat. No. 5,122,136) as was discussed above.

Guglielmi et al. shows an embolism-forming device and procedure for using that device. Specifically, Guglielmi et al. fills a vascular cavity such as an aneurysm with an embolic device such as a platinum coil which coil has been endovascularly delivered. The coil is then severed from its insertion tool by the application of a small electric current. Desirably, the insertion device involves a guidewire which is attached at its distal end to an embolic device by an electrolytic, sacrificial joint. Guglielmi et al. suggests that when the embolic device is a platinum coil, the platinum coil may be 1–50 cm. or longer as is necessary. Proximal of the embolic coil is a guidewire, often stainless steel in construction. The guidewire is used to push the platinum embolic coil, obviously with great gentleness, into the vascular site to be occluded. The patent shows a variety ways of linking the embolic coil to the pusher guidewire. For instance, the guidewire is tapered at its distal end and the distal tip of the guidewire is soldered into the proximal end of the embolic coil. Additionally, a stainless steel coil is wrapped coaxially about the distal tapered portion of the guidewire to provide column strength to the guidewire. This coaxial stainless steel wire is joined both to the guidewire and to the embolic coil. Insulation may be used to cover a portion of the strength-providing stainless steel coil. This arrangement provides for two regions which must be electrolytically severed before the embolic coil is severed from the guidewire.

A further variation of the Guglielmi detachable coil is one in which the distal tip of the stainless steel guidewire is not soldered to the proximal end of the embolic device. A simple conical stainless steel wire is included from the stainless steel guidewire to the embolic coil.

A further variation found in Guglielmi et al. includes a thin, threadlike extension between the guidewire core and the proximal end of the embolic coil. In this way, the guidewire does not extend to the embolic coil, but instead relies upon a separately introduced extension.

A continuation-in-part application to the Guglielmi et al patent discussed above Ser. No. 840,211, filed on 24 Feb. 1992, now U.S. Pat. No. 5,354,295 entitled "IMPROVEMENTS IN AN ENDOVASCULAR ELECTROLYTICALLY DETACHABLE WIRE AND TIP FOR THE FORMATION OF THROMBUS IN ARTERIES, VEINS, ANEURYSMS, VASCULAR MALFORMATIONS AND ARTERIOVENOUS FISTULAS" describes the use of mechanically detachable embolic devices as well as those which are electrolytically detachable. The embolic devices may be augmented with attached filaments.

Dr. Taki has devised a variation of the Guglielmi detachable coil using a copper link between the guidewire and the coil.

None of the noted procedures using electrolytically detachable embolic devices suggests the concept of limiting the size of the sacrificial link to allow more precise placement of the embolic device and facile, quick detachment.

SUMMARY OF THE INVENTION

As noted above, this invention is a device for forming a vascular occlusion at a selected site. Generally, the device comprises a guidewire having a distal tip which distal tip may be introduced into the selected vascular site or cavity. The guidewire is joined to the distal tip or embolic device in such a way that the vascular device may be electrolytically detached by application of a current to the core or guidewire. The improvement involves the use of a discrete, sacrificial link between the core wire and the vascular device to allow clean and quick detachment from the guidewire. The focussed electrolysis found at the sacrificial site reduces the overall possibility of occurrence of multiple electrolysis sites and liberation of large particles from those sites.

There are several variations of the sacrificial joint involving extensive electrical insulation about the core wire and any supporting coil devices or the use of direct coating on electrolytically susceptible surfaces.

DESCRIPTION OF THE INVENTION

Each of the discrete sacrificial joints discussed below may be used in the device shown in U.S. Pat. No. 5,122,136 to Guglielmi et al., the entirety of which patent is incorporated by reference.

Figure 1:
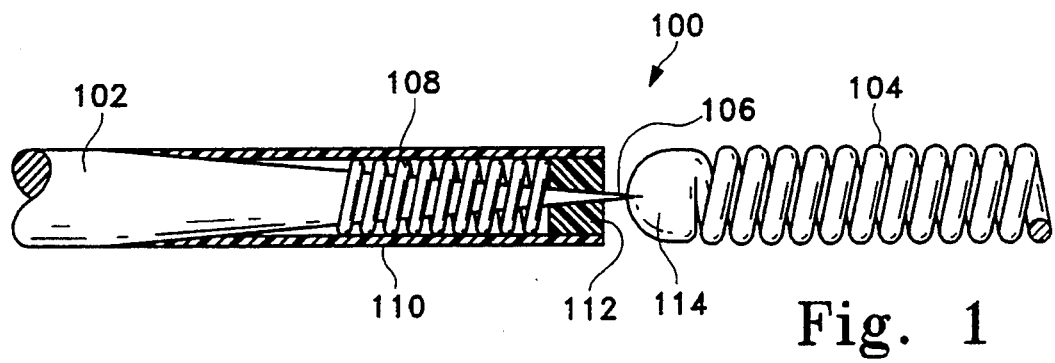
FIGS. 1, 2, 3, 5, and 6 show sideview, partial cross-sectional views of variations of the inventive, electrolytically susceptible, sacrificial link between a core wire and an embolic device.

The first of such variations is shown in FIG. 1. The assembly 100 is made up generally of a guide or core wire 102 which tapers at its distal end to a point and is soldered into the proximal end of a vasoocclusive device 104, which in this case is a coil. All of the core wire 102 is covered with an insulating material such as Teflon ®, polyurethane, polyethylene, polypropylene, or other suitable polymeric material, except the most distal exposed joint or sacrificial link 106. Link 106 is not coated with an electrical insulator and is of a material which is susceptible to electrolytic dissolution in blood. The core wire 102 is typically stainless steel and may be disposed within a protective catheter not shown. Stainless steel guidewire 102 typically is approximately 10-30 mils. in diameter. Often the guidewire is 50-300 cm. in length, that is to say, from the entry site outside the body to sacrificial link 106.

Sacrificial link 106 is a discrete link. By "discrete" we mean to say preferably that the joint is substantially dissolved upon release of the vasoocclusive device 104. Alternatively, "discrete" may be meant to mean that the length of the link 108 is no greater than the diameter of the sacrificial link 106 or that the electrolytic surface present after the vasoocclusive device is released is not substantially greater than would be a circle having the diameter of the sacrificial link 106.

Also shown in FIG. 1 is a coil 108 which is soldered at its proximal end and, typically, is designed to provide some column strength to the guidewire assembly while not detrimentally affecting the flexibility of the tapered portion of the core wire 102. Obviously, in the area where the support coil 108 is soldered to core wire 102, the coating on 102 is not present so to allow the solder to adhere to metal surfaces. Further, on the distal tip of core wire 102 may be found a pair of insulators: sleeve 110 and end plug 112 which serve to further remove the stainless steel coil 108 from contact with the blood while the step of electrolytic detachment is carried out. Preferably, the end plug 112 and sleeve 110 are adhesively attached to each other so to form an electrically insulating or electrolysis-tight housing about coil 108. The end plug 112 and sleeve 110 form a planar surface in the Figure which is generally planar and perpendicular to the axis of the core wire 102.

As noted above, the distal end of guidewire or core wire 102 is inserted into the solder joint 114 forming the proximal end of vasoocclusive device 104.

As will be discussed in more detail below, the discrete sacrificial link 106 is completely or substantially completely dissolved during electrolysis.

Figure 2:
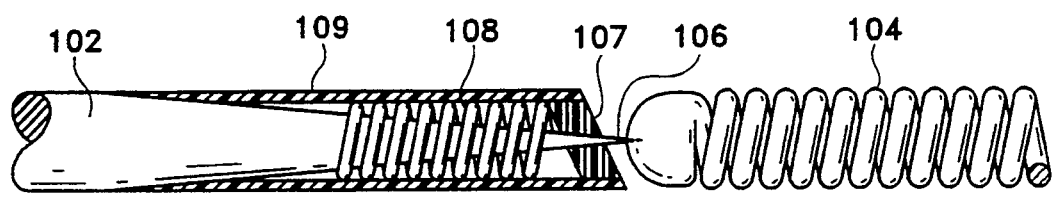

FIG. 2 shows a most preferred variation of the FIG. 1 device having a guide or core wire 102 which may taper at its distal end to a point and which is soldered into the proximal end of a vasoocclusive device 104, which in this case is a coil. Similarly, the distal portion of the guidewire 102 having stainless steel coil 108 thereabout is all enclosed in an end plug 107 and sleeve 109 to provide additional protection to the guidewire and included stainless steel coil 108. The major difference between the FIG. 1 device and the link assembly shown in FIG. 2 is the use of a bias formed distal region. The combination of end plug 107 and sleeve 109 allow clear access by blood (and therefore electrolytic current) to the sacrificial link (106). The end plug 112 and sleeve 110 form a planar surface in the Figure which is generally planar but not perpendicular to the axis of the core wire 102.

Obviously, the shape of the surface is, in and of itself, of much criticality except to the extent it allows reasonably free access of the blood to the sacrificial joint 106. Curved, slotted, and other variations of the end surface are also contemplated in this invention.

Figure 3:
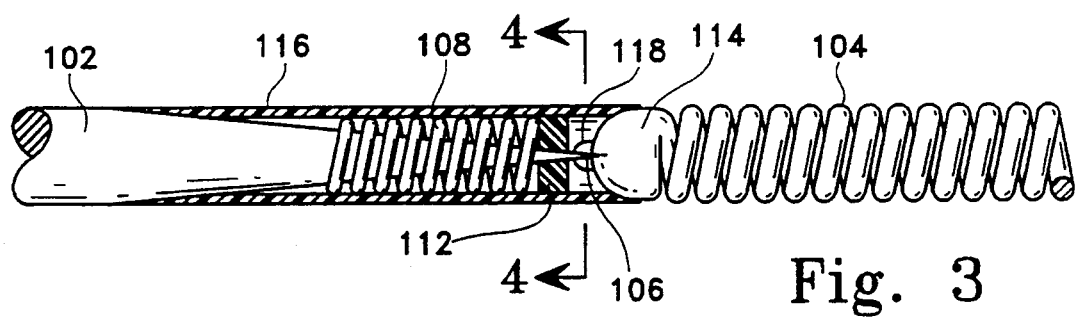
Figure 4:
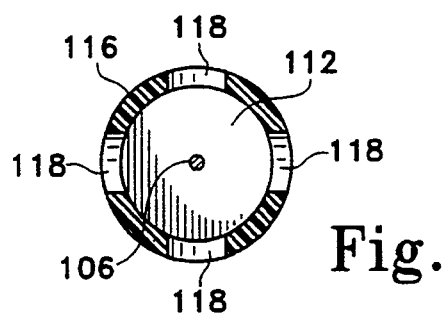
FIG. 4 shows a cross section of the variation shown in FIG. 3.

FIG. 3 shows a variation of the device shown in FIGS. 1 or 2 in that the core wire 102 comes down to a point having a sacrificial link 106 which is soldered into solder joint 114 in vasoocclusive device 104. The coil 108 provided to give additional column strength to the core wire 102 is also present. End plug 112 is also found in this device. The variation is in the outer sleeve 116. In this variation, the outer sleeve extends up to and is in contact with the solder joint 114 found at the end of vasoocclusive device 104. To allow the sacrificial link 106 to have electrical contact with the patient's blood, a sleeve 116 has a number of openings therein to allow contact of the blood with the sacrificial link 106. The openings 118 may be seen both in FIG. 3 and in a cross-section found in FIG. 4. The end plug 112 and the cross-section of the sacrificial link 106 may also be seen in FIG. 4. The variation shown in FIG. 3 may have slightly more physical strength but because of the smaller area through openings 118, the step of electrolysis may be slightly slower.

Figure 5:
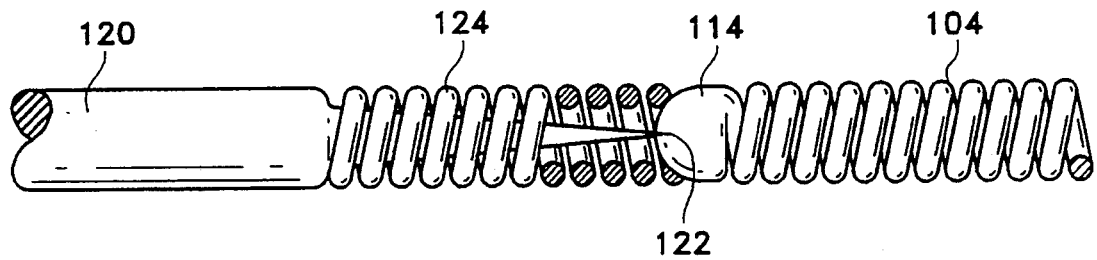

FIG. 5 shows another variation of the inventive sacrificial joint. The device again has a guidewire or core wire 120 which tapers down to a small point which is soldered into solder joint 114 on the end of vasoocclusive device 104. Again, as with the device in FIGS. 1, 2, and 3, all except the most distal portion 122 of core wire 120 is coated with an insulating material such as Teflon ®  polymer or other suitable insulating polymers. In this instance, however, the sacrificial link 122 forming the distal end of core wire 120 is surrounded, as is a portion of the taper on guidewire 120 with a release spring 124. Release spring 124 is attached to the guidewire body 120 but is not attached to the solder joint 114 on vasoocclusive device 104. The release spring 124 is slightly compressed. It, however, has some space between its adjacent windings as it is found in place on the core wire 120. In this way, blood has access to sacrificial link 122 between the adjacent windings on release spring 124. When the sacrificial link 122 is dissolved, release spring 124 gently pushes vasoocclusive device 104 away from the tip of the guidewire or core wire 120. Release spring 124 is completely insulated except, obviously, for the portion which is connected to the core wire 120, if welding or soldering of release spring 124 is had to core wire 120.

Figure 6:
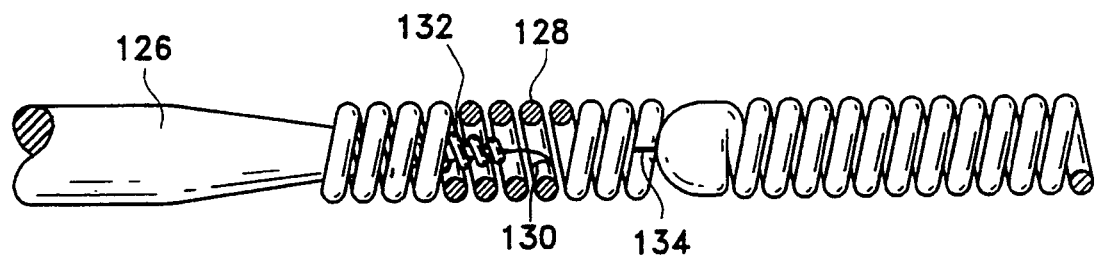
Figure 7:
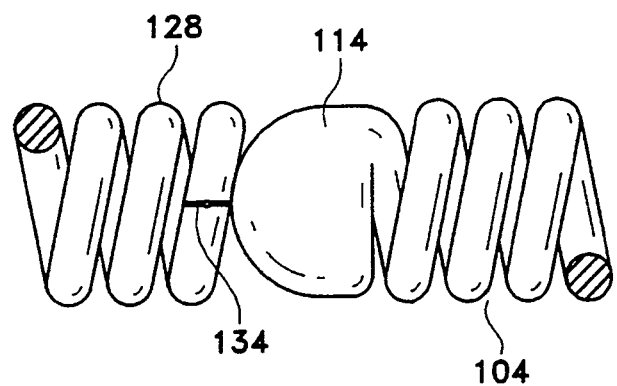
FIG. 7 shows a close up side view of a variation such as found in FIG. 6.

FIG. 6 shows a variation of the inventive device in which core wire 126 tapers down and is either directly soldered to the interior of coil 128 at solder joint 130 or is connected to a link which is then soldered at joint 130. A support spring 132 interior to coil 128 may be used in the same way as was shown in FIGS. 1, 2, and 3. As a safety factor, coil 128 and support spring 132 are fixed to core wire 126. The coil 128 is also electrically connected to core wire 126. All of core wire 126, coil 128, and support spring 132 are insulated so as to prevent electrolysis upon application of voltage to core wire 126. The exception to this insulation is a scribe or score mark 134 which forms the discrete sacrificial link. Score mark 134 is shown in more detail on FIG. 7. Again, the effect of the scribe or score mark 134 as shown in FIG. 6 is that the electrolysis takes place only at that small area and when the electrolysis has completely severed coil 128 at that point, there is little potential for electrolysis to take place at any other site on the core wire 126 or spring 128.

Vasoocclusive device 104 is shown in each of the drawings above to be a coil. It may be a coil or a braid or other vasoocclusive device as is already known. The vasoocclusive device may be covered or connected with fibrous materials tied to the outside of the coil or braided onto the outer cover of the coil as desired. Such fibrous adjuvants may be found in U.S. patent application Ser. No. 07/965,973, to Phelps et al, or in U.S. patent application Ser. No. 07/771,013, entitled "Vasoocclusion Coil with Attached Fibrous Elements", the entirety of which are incorporated by reference.

Figure 8:
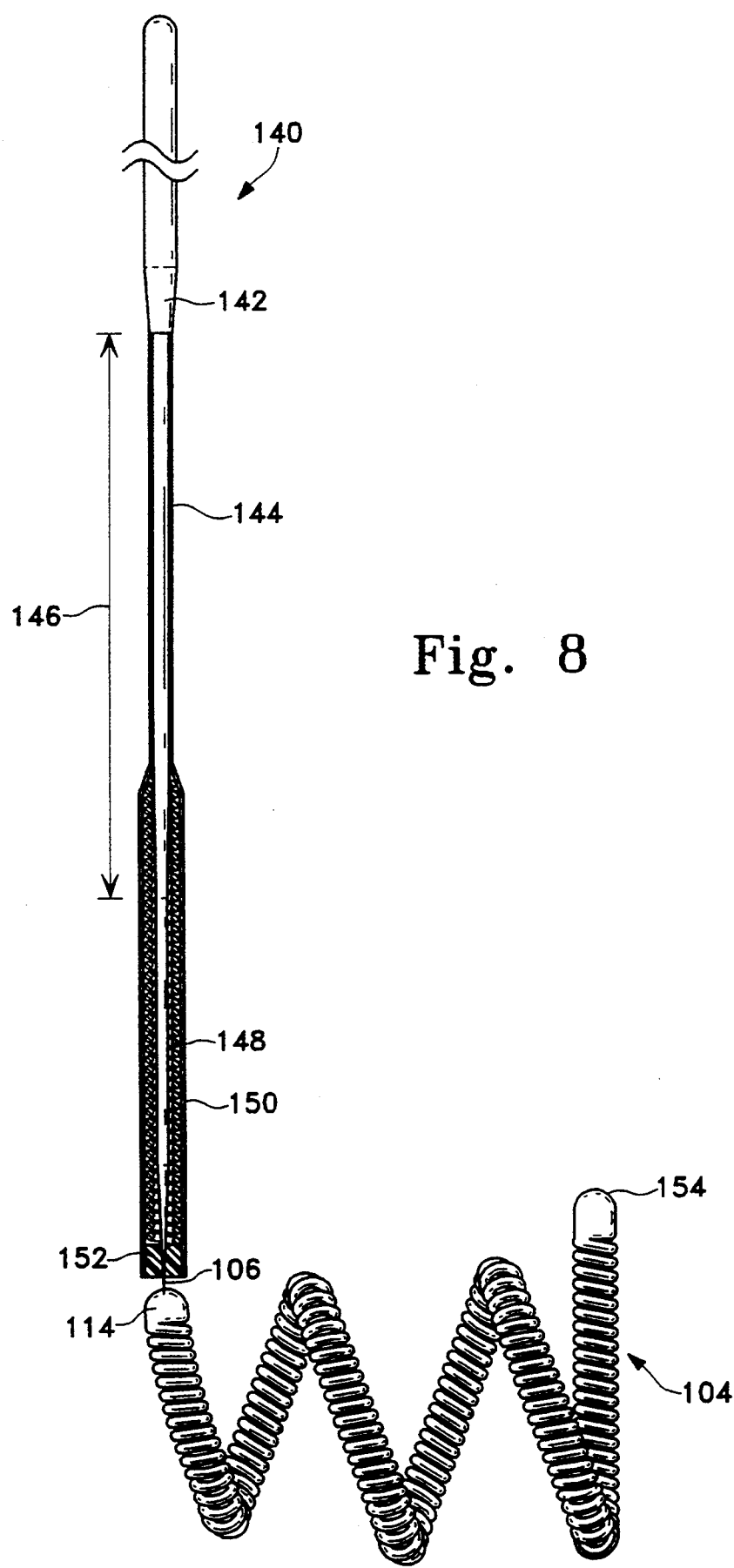
FIG. 8 shows side view of a typical assembly involving the inventive sacrificial link used in this invention.

FIG. 8 shows a typical layout involving the inventive discrete sacrificial joint 106 as was generally shown in the Figures above. In FIG. 8, a somewhat conventional Teflon ® laminated or similarly insulated stainless steel guidewire assembly 140 may be placed within a protective catheter. As was noted above, stainless steel guidewire 140 may have a diameter of approximately 10–30 mils. In the noted embodiment in FIG. 8, guidewire assembly 140 is tapered at its distal end to form a conical section 142 which joins a further section 144 which extends along a length of guidewire 146. Section 144 then gradually narrows down to a thinner section 148. The guidewire assembly 140, as noted above, may be placed within a catheter body and is typically 50–200 cm. in length down to sacrificial link 106. As was shown in FIG. 1, the distal section of guidewire assembly 140 has an outer Teflon ® sleeve 150 (or sleeve of other appropriate insulating material). Furthermore, it has an end plug 152 to permit isolation of the guidewire electrically from the blood except at sacrificial discrete link 106. The proximal end of vasoocclusive device 104 is typically a soldered tip or a joint 114. Preferably, vasoocclusive device 104, when a coil, forms a secondary loop after it emanates from the end of the catheter. The distal end of vasoocclusive device 104 may also have an end plug or tip to prevent punctures of the aneurysm when introduced into the aneurysm sac.

As noted, the coil or vasoocclusive device 104 may be pre-biased to form a cylinder or conical envelope. However, the vasoocclusive device 104 is extremely soft and its overall shape is easily deformed. When inserted within the catheter (not shown), the vasoocclusive device 104 is easily straightened so to lie axially within the catheter. Once ejected from the tip of the catheter, vasoocclusive device 104 may form a shape shown in FIG. 8 or may be loosely deformed to conform to the interior shape of the aneurysm.

Figure 9:
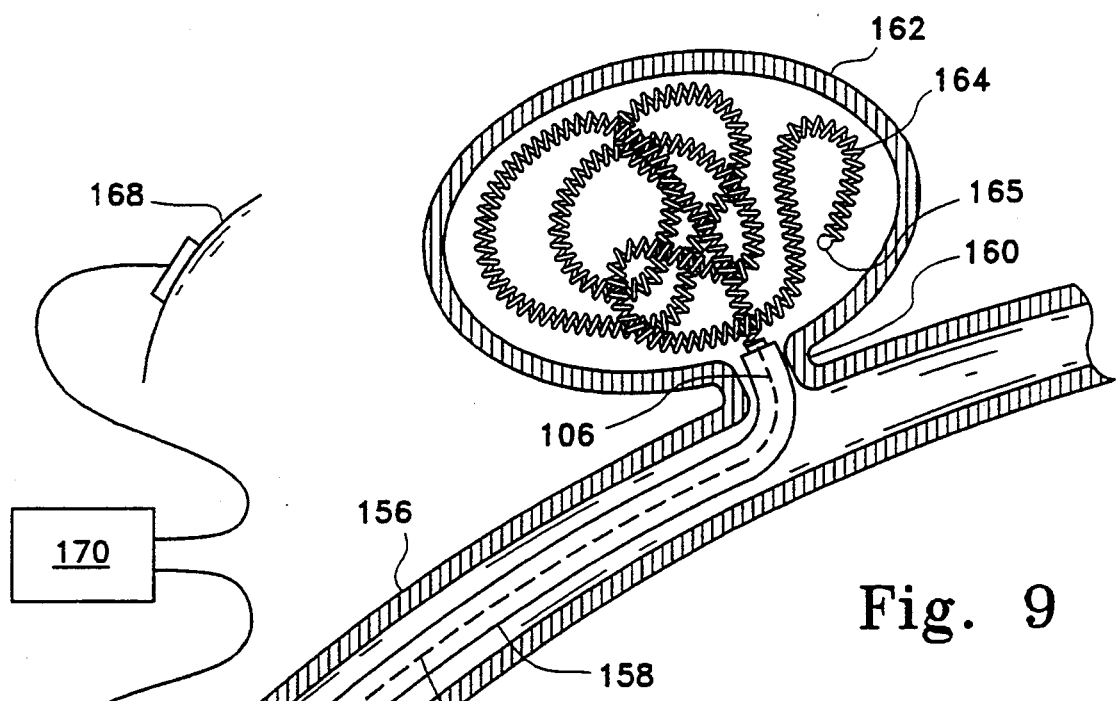
FIGS. 9 and 10 schematically depict the method for deploying the vasoocclusive device using the inventive sacrificial link.

FIG. 9 shows the placement of the inventive devices shown above within a vessel 156 with the tip of catheter 158 placed near neck 160 of aneurysm 162. Vasoocclusive device 164 is fed into aneurysm 162 at least until sacrificial link 106 is exposed beyond the distal tip of the catheter 158. A positive electric current of approximately 0.01–2 milli-amps at 0.1–6 volts is applied to guidewire 166 to form a thrombus within aneurysm 162. The negative pole 168 of power supply 170 is typically placed in electrical contact with the skin.

After the thrombus has been formed and the aneurysm occluded, vasoocclusive device 164 is detached from guidewire 166 by electrolytic disintegration of sacrificial link 106.

Figure 10:
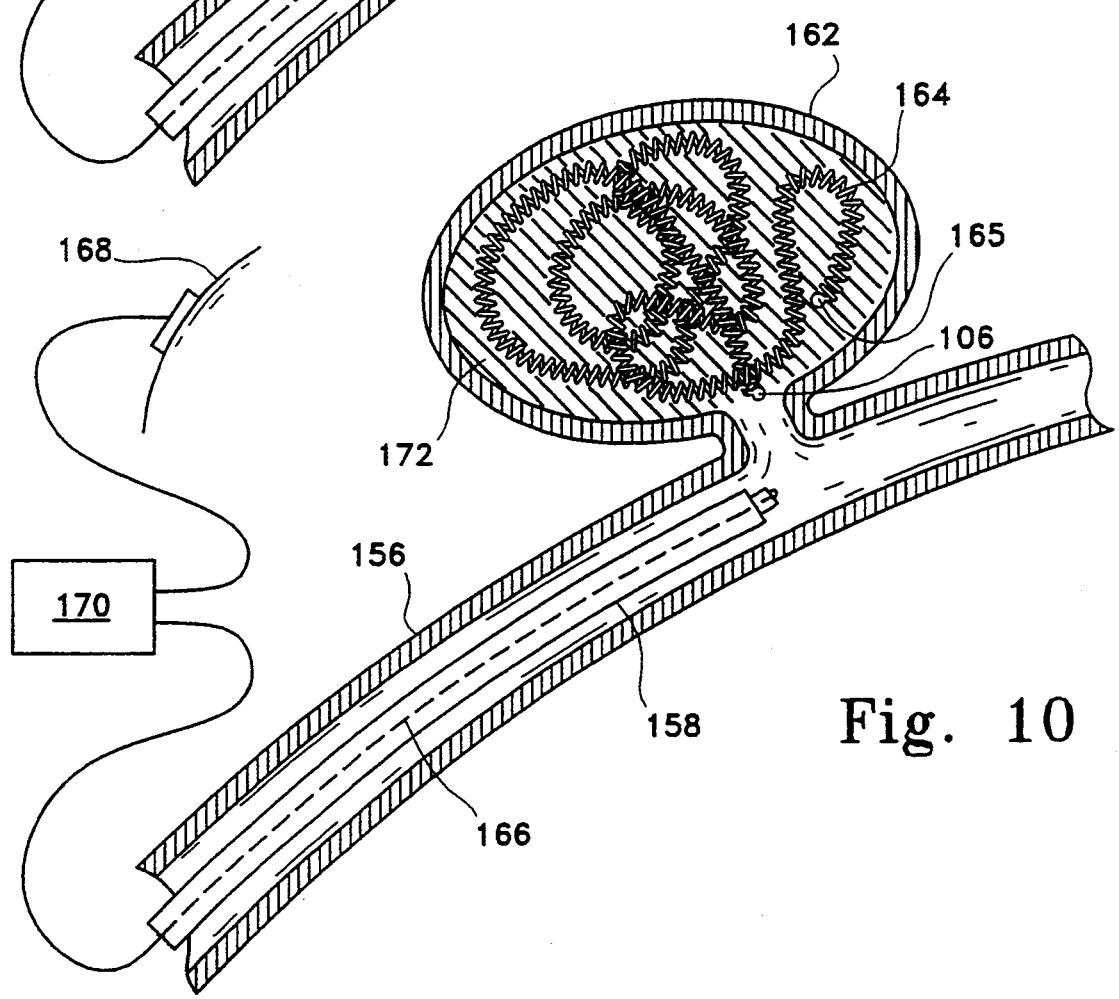

After sacrificial link 106 is completely dissolved by electrolytic action, typically within 3–10 minutes, the guidewire 166, catheter 156, are removed vessel 156, leaving aneurysm 162 occluded as shown in FIG. 10.

The process is typically practiced under fluoroscopic control with local anesthesia. A transfemoral catheter is utilized to treat a cerebral aneurysm and is usually introduced at the groin. When the vasoocclusive device 164 is platinum, it is not effected by electrolysis. When the guidewire and pertinent portions of the supporting coils at the distal tip of the guidewire are adequately coated with insulating coverings, only the exposed portion at the sacrificial link 106 is effected by the electrolysis.

Many alterations and modifications may be made by those having ordinary skill in the art without departing from the spirit and scope of the invention. Therefore, it must be understood that the shape of the tip or distal platinum coil used in combination with the guidewire according to the invention may be provided with a variety of shapes and envelopes.

The illustrated embodiments have been used only for the purposes of clarity and should not be taken as limiting the invention as defined by the following claims.

We claim as our invention:

1. A guidewire for use in the formation of a vascular occlusion, in combination with a catheter, comprising:
   a core wire, said core wire having an axis and not being susceptible to electrolytic disintegration in blood,
   a discrete, sacrificial, severable link susceptible to electrolytic disintegration in blood distal to and severably connected to said core wire, and
   an elongate tip portion extending distally beyond said core wire and adapted to form said occlusion at a selected site within a mammal vasculature, said elongate tip portion not being susceptible to electrolytic disintegration in blood and severable from the core wire upon electrolytic disintegration of the sacrificial link.

2. The guidewire of claim 1 wherein the core wire is insulated proximally to the discrete, sacrificial link with a polymer.

3. The guidewire of claim 2 wherein the polymer is selected from polyfluorocarbon, polyethylene, polypropylene, polyurethane, and silicone polymers.

4. The guidewire of claim 2 wherein the polymeric insulation is a sleeve.

5. The guidewire of claim 2 wherein the insulation is coated directly onto the core wire.

6. The guidewire of claim 1 wherein the elongate tip section is a coil.

7. The guidewire of claim 6 wherein the elongate tip section comprises a platinum alloy coil.

8. The guidewire of claim 1 wherein the core wire is electrically connected to a coil located coaxially about the axis of the core wire and which is electrically insulated from surrounding blood.

9. The guidewire of claim 8 wherein the discrete sacrificial link is a section of the coaxial coil having a score in the insulation on the coaxial coil.

10. The guidewire of claim 2 wherein the core wire, proximally of the discrete, sacrificial link is insulated using a sleeve coaxial to the core wire and having an open distal end which sleeve distal end is closed with a plug adjacent the sacrificial link and coaxial to the core wire.

11. The guidewire of claim 10 wherein the distal end of the sleeve and plug adjacent the sacrificial link define a planar surface.

12. The guidewire of claim 11 where the planar surface is generally perpendicular to the axis of the core wire.

13. The guidewire of claim 11 where the planar surface is not generally perpendicular to the axis of the core wire.

* * * * *

UNITED STATES PATENT AND TRADEMARK OFFICE
CERTIFICATE OF CORRECTION

PATENT NO. : 5,423,829
DATED : June 13, 1995
INVENTOR(S) : PHAM et al

It is certified that error appears in the above-indentified patent and that said Letters Patent is hereby corrected as shown below:

*column 1, line 55:* change "4,884,525" to --4,884,579 --.

Column 7, claim 1, delete claim 1 and insert the following:

1. A guidewire for use in the formation of a vascular occlusion, in combination with a catheter, comprising:

a core wire, said core wire having an axis and not being susceptible to electrolytic disintegration in blood, a discrete, sacrificial, severable link having a diameter and which is susceptible to electrolytic disintegration in blood distal to and severably connected to said core wire wherein said link has a length no greater than the diameter of the link or that the surface of the link after disintegration is not substantially greater than would be a circle having the diameter of the link, and

UNITED STATES PATENT AND TRADEMARK OFFICE
CERTIFICATE OF CORRECTION

PATENT NO. : 5,423,829
DATED : June 13, 1995
INVENTOR(S) : PHAM, et al

It is certified that error appears in the above-indentified patent and that said Letters Patent is hereby corrected as shown below:

cont.

an elongate tip portion extending distally beyond said core wire and adapted to form said occlusion at a selected sire within a mammal vasculature, said elongate tip portion not being susceptible to electrolytic disintegration in blood and severable from the core wire upon an electrolytic disintegration of the sacrificial link.

Signed and Sealed this

Twenty-fifth Day of June, 1996

Attest:

BRUCE LEHMAN

*Attesting Officer*   *Commissioner of Patents and Trademarks*

UNITED STATES PATENT AND TRADEMARK OFFICE
CERTIFICATE OF CORRECTION

PATENT NO. : 5,423,829
DATED : June 13, 1995
INVENTOR(S) : Pham, et. al.

It is certified that error appears in the above-indentified patent and that said Letters Patent is hereby corrected as shown below:

In the Certificate of Correction that issued May 28, 1996, in Column 7, claim 1, change "sire" to --site--.

Signed and Sealed this

Nineteenth Day of November, 1996

Attest:

BRUCE LEHMAN

Attesting Officer         Commissioner of Patents and Trademarks